United States Patent [19]

Akahira et al.

[11] 4,284,427
[45] Aug. 18, 1981

[54] HERBICIDAL COMPOSITION FOR PADDY FIELDS

[75] Inventors: Rokuro Akahira, Higashikurume; Shinzo Someya, Tokorozawa, both of Japan

[73] Assignee: Kanesho Company Limited, Tokyo, Japan

[21] Appl. No.: 96,976

[22] Filed: Nov. 23, 1979

[51] Int. Cl.³ .................... A01N 43/70; A01N 37/46
[52] U.S. Cl. .......................................... 71/93; 71/111; 71/DIG. 1
[58] Field of Search .................................... 71/93, 111

[56] References Cited

U.S. PATENT DOCUMENTS 3,393,991  7/1968  Hamm ....................................... 71/93

FOREIGN PATENT DOCUMENTS

| | | | |
|---|---|---|---|
| 46679 | 9/1972 | Australia ..................................... | 71/111 |
| 751164 | 11/1970 | Belgium ....................................... | 71/93 |
| 50-42047 | 4/1975 | Japan .......................................... | 71/93 |
| 50-117937 | 9/1975 | Japan .......................................... | 71/93 |
| 51-12931 | 1/1976 | Japan .......................................... | 71/93 |
| 960649 | 6/1964 | United Kingdom ........................ | 71/93 |

*Primary Examiner*—Glennon H. Hollrah
*Attorney, Agent, or Firm*—Murray and Whisenhunt

[57] ABSTRACT

A herbicidal composition for paddy fields is provided by the present invention, which contains as active ingredients a mixture or a combination of N-chloroacetyl-N-(2,6-diethylphenyl)-glycineethylester and 2,4-bis(ethylamino)-6-methylthio-1,3,5-triazine. This composition exhibits synergistic herbicidal effect against various weeds grown in paddy fields, during the period of from the time of their germination up to the growing stage.

16 Claims, No Drawings

HERBICIDAL COMPOSITION FOR PADDY FIELDS

The present invention relates to and provides a herbicidal composition for the paddy fields which contains as active ingredients a mixture of N-chloroacetyl-N-(2,6-diethylphenyl)-glycineethylester and 2,4-bis (ethylamine)-6-methylthio-1,3,5-triazine, and which has herbicidal effect against various weeds during the period of from the time of germination up to the growing stage. The present herbicidal composition has very high usefulness due to drastically extended period of time for the appropriate application. The present invention also provides a method of controlling weeds grown in paddy fields by the couse of both active chemicals.

The range of the germination period of almost all the weeds in paddy fields is so wide, starting from the puddling and leveling, that it is very difficult to determine the appropriate application period for controlling weeds. For the weed control in the paddy field the most appropriate and recommendable application time is at the time of uniform growth stage of the weeds.

However, practically speaking, it is very difficult for most farmers to determine such a proper application time for paddy field weed control and furthermore from the aspect of labor there still remains some problem in losing such application time. Accordingly, such herbicides with a long application period have been expected for a long time.

The inventors of this invention have found that the above new herbicidal composition can meet the above requirements due to the synergistic effect obtained from combining N-Chloroacetyl-N-(2,6-diethylphenyl)-glycineethylester and 2,4-bis (ethylamino)-6-methylthio-1,3,5-triazine (the latter being hereafter referred to as Simetryne). The favourable mixing ratio of the both chemicals is in the range of 1:10-10:1 and more preferably, 1:2-3:1 because the appropriate dosage of the active ingredients per are 1.0-30.0 g/a, preferably 4.0-12.0 g/a of N-Chloroacetyl-N-(2,6-diethylphenyl)-glycineethylester and 3.0-10.0 g/a, preferably 4.0-8.0 g/a of Simetryne, thereby attaining excellent effects. Thus, the total dosage with the above preferable mixing ratio, for example, those ranging from 8 g/a (4 g of N-Chloroacetyl-N-(2,6-diethylphenyl)- glycineethylester +4 g of Simetryne) to 20 g/a (12 g of N-Chloroacetyl-N-(2,6-diethylphenyl)-glycineethylester +8 g of Simetryne) will present satisfactory result.

Practically, e.g. in case of granular formulation, 3.5 W/W% of the active component mixture of N-Chloroacetyl-N-(2,6-diethylphenyl)-glycineethylester and Simetryne in the above ratio is milled with 96.5 W/W% of a mixture of dispersant, carrier and the like and then mixed with some water, and thereafter they are kneaded together and granulated by means of a granulating machine and followed by drying to make granular agent.

Moreover, it is applicable in the form of a wettable powder (W.P.). For instance, 35 W/W% of the mixture in the above ratio of N-Chloroacetyl-N-(2,6-diethylphenyl)-glycineethylester and Simetryne is mixed with 65 W/W% of carrier mixture and formulated in wettable powder.

2,4-bis (ethylamino)-6-methylthio-1,3,5-triazine which is one of the compornents of the present composition is a herbicide with so-called "root uptaking" type herbicidal characteristics, which kill weeds by interferring with photosynthesis and control their germination too. From the viewpoint of the leaf stage of weeds, the range of the most appropriate application time during which Simetryne exhibit a high efficacy, for example, against *Echinochloa Crus-galli* is from its germination to the one leaf stage, but any practical effect cannot be expected thereby after the 3 leaf stage. Moreover, it is known that the application of Simetryne at a high temperature often results in phytotoxicity to the rice plants. Within the Japanese teritory, especially in West-South areas the application of Simetryne is known to have a lot of limitations due to their warm climate.

On the other hand, it is known that N-Chloroacetyl-N-(2,6-diethylphenyl)-glycineethylester is uptaken from the root or new leaves. The synergistic effect from the combination of N-Chloroacetyl-N-(2,6-diethylphenyl)-glycineethylester, having relatively analogous actions to those of Symetryne, and Simetryne was unexpected and special features brought about by the mixing effect should be noted.

More concretely speaking, there have been difficulties in control the already grown weeds by means of the existing herbicides. However, the present new herbicidal composition has been found to exhibit extremely good control in applying at any time during the period from the transplanting time to 20 days after transplanting. Especially remarkable control of *Echinochloa Crusgalli* in the 2 to 3 leaf stages, which was considered very difficult, has been accomplished. And furthermore, it showed extremely complete control of *Eleocharis acicularis*, though it is difficult with Simetryne alone to control such perennial weed as *Eleocharis acicularis*. Due to the drastic decrease in the dosage of Simetryne, the present herbicidal composition decreases the possibilities of phytotoxicity by Simetryne and it is also a great advantage thereof to be able to use it at any time during the period of from transplanting up to the later stages of the rice plant. The characteristic herbicidal effect of the present composition is illustrated by the following comparative examples including the experimental data. (% shows weight % of weeds)

EXPERIMENT I

*Eleocharis acicularis* at germination, Echinochloa at the one-leaf stage, Echinochloa at the two leaf stage and rice plant at the three leaf stage were prepared in a 15-diameter pot and submerged 3 cm deep in water. Then Simetryne single granular, the N-Chloroacetyl-N-(2,6-diethylphenyl)-glycineethylester single granular and the mixed agent of both components were applied.

The observation was made 15 days after the treatment as to the weight of the remaining *Echinochloa Crus-galli* and *Eleocharis acicularis* and phytotoxicity to the rice plant.

The results of the experiment are shown in Table I.

In the table, PG shows N-Chloroacetyl-N-(2,6-diethylphenyl)-glycineethylester.

TABLE I

| Experimental Chemicals | Dosage (amounts of components) g/a | *Eleocharis acicularis* | Weight of of *Echinochloa Crus-galli* One leaf stage | Weight of of *Echinochloa Crus-galli* Two leaves stage | Phytotoxicity to rice |
|---|---|---|---|---|---|
|  | 8 | 10 | 29 | 21 | — |
| PG | 4 | 26 | 48 | 48 | — |
|  | 2 | 40.1 | 51 | 54 | — |
|  | 1 | 58.5 | 54 | 78 | — |
|  | 4.5 | 9 | 0 | 11 | ± |

TABLE I-continued

| Experimental Chemicals | Dosage (amounts of components) g/a | Eleocharis acicularis | Weight of of Echinochloa Crus-galli | | Phytotoxicity to rice |
|---|---|---|---|---|---|
| | | | One leaf stage | Two leaves stage | |
| Simetryne | 4.5 × 1 | 33 | 3 | 43 | — |
| | 4.5 × ½ | 64 | 72 | 100 | — |
| | 4.5 × ¼ | 88 | 94 | 100 | — |
| | 8 + 4.5 | 0 | 0 | 0 | ± |
| PG + | $\frac{8 + 4.5}{2}$ | 0 | 0 | 8 | — |
| Simetryne | $\frac{8 + 4.5}{4}$ | 2.0 | 11 | 18 | — |
| | $\frac{8 + 4.5}{8}$ | 8.5 | 19 | 24 | — |

*The figures in Columns 3–5 show % un-treated plot.

EXPERIMENT II

The composition containing PG (2%) +Simetryne (1.5%) were applied at the dosage of 2 kg/10 a, 3 kg/10 a, 4 kg/10 a, to the paddy field (10 m² per plot 20 days after transplanting. And the observation on weeds was made 30 days after the treatment.

The results are shown in Table II.

TABLE II

| | Dosage (Product base) kg/10a | Weight of dried weeds | | | | Phytotoxicity to rice |
|---|---|---|---|---|---|---|
| | | Ecinochloa Crus-galli | Cyperus Microiria Steud | Monochoria Vaginalis | Eleocharis Acicularis | |
| PG (2%) | 2 | 0 | 0 | 0 | 2.3 | — |
| + | 3 | 0 | 0 | 0 | 0 | — |
| Simetryne (1.5%) | 4 | 0 | 0 | 0 | 0 | — |
| MO | 2 | 83 | 56 | 41 | 62 | — |
| | 4 | 45 | 23 | 17 | 34 | ± |

*MO: 2,4,6-Trichlorophenol-4'-nitrophenylether

As clear from the above results, when compared with the respective single component herbicide and MO granular which is widely used by the farmers, the herbicidal effect of the present herbicidal composition is conspicuously improved in controling the grown weeds even 20 days after transplanting. Furthermore, in view of expansion of the application period of time, even if the transplanting day is postponed by about 10–20 days, the present herbicidal composition is not lost in its herbicidal effect, and consequently it will largely contribute to save the farmers labor.

As mentioned before, the active ingredients of the present herbicidal composition are N-Chloroacetyl-N-(2,6-diethylphenyl)-glycineethylester and Simetryne. Though the present composition can drastically decrease the quantity of each chemical component, as compared with each single component, the desirable range of the mixing ratio is such that when the present composition has been applied to paddy fields there is present 1.0–30.0 g/a, more preferably 4.0–10.0 g/a of N-Chloroacetyl-N-(2,6-diethylphenyl)-glycineethylester and 3.0–10.0 g/a, more preferably 4.0–8.0 g/a of Simetryne.

The following examples illustrate the practical formulations of the present herbicidal composition.

EXAMPLE I

| | |
|---|---|
| N-Chloroacetyl-N-(2,6-diethylphenyl)-glycineethylester | 2.0 W/W% |
| Simetryne | 1.5 W/W% |
| Sodium lignosulfonate | 2.0 W/W% |
| White Carbon | 5.0 W/W% |
| Bentonite | 89.5 W/W% | were mixed and powdered uniformly and kneaded with some water and then formulated in granular after drying.

EXAMPLE II

| | |
|---|---|
| N-Chloroacetyl-N-(2,6-diethylphenyl)-glycineethylester | 20.0 W/W% |
| Simetryne | 15.0 W/W% |
| Emal 40 (Kao-Atlas Co. Ltd., Fatty alcohol sulfate) | 2.0 W/W% |
| Demol-N (Kao-Atlas Co. Ltd., Dinaphthylmethane disulfide) | 2.0 W/W% |
| White Carbon | 10.0 W/W% |
| Clay | 51.0 W/W% | were mixed and powdered and then formulated in wettable powder.

EXAMPLE III

| | |
|---|---|
| N-Chloroacetyl-N-(2,6-diethylphenyl)-glycineethylester | 20 W/W% |
| Simetryne | 15 W/W% |
| Newkalgen-705 (Takemoto Co. Ltd.) POE alkyl aryl ether POE alkyl ether Ca-alkylaryl sulfonate | 6 W/W% |
| Xylene | 59 W/W% | were mixed and then formulated in emulsifiable concentrate.

We claim:

1. A herbicidal composition, consisting essentially of an effective amount of a mixture of, as active ingredients, N-chloroacetyl-N-(2,6-diethylphenyl)-glycineethylester and 2,4-bis(ethylamino)-6-methylthio-1,3,5-triazine in a weight ratio of 1:1–3:1, respectively.

2. The composition according to claim 1 in which the weight ratio of N-chloroacetyl-N-(2,6-diethylphenyl)-glycineethylester to 2,4-diethylamino-6-methylthio-1,3,5-triazine is about 8:4.5.

3. The composition according to claim 1 or 2 which is prepared in the form of a granular agent.

4. The composition according to claim 3 which consists essentially of the two active ingredients, dispersant(s) and inert carrier(s).

5. The composition according to claim 4 in which the dispersant is sodium lignosulfonate and the carriers are white carbon and bentonite.

6. The composition according to claim 1 or 2 which is prepared in the form of a wettable agent.

7. The composition according to claim 6 which consists essentially of the two active components, surfactant(s) and inert carrier(s).

8. The composition according to claim 7 in which the surfactant is a fatty alcohol sulfate and dinaphthylmethane disulfide, and the carrier is white carbon.

9. The composition according to claim 1 or 2 which is prepared in the form of an emulsifiable concentrate.

10. The composition according to claim 9 which consists essentially of the two active components, an emulsifier and a solvent.

11. The composition according to claim 10 in which the emulsifier is a mixture of POE derivatives and alkylaryl sulfonate and the solvent is xylene.

12. A method of controlling weeds in paddy fields, said method comprising applying to said fields an effective amount of the composition of claim 1.

13. Method of claim 12, wherein the weight ratio of N-chloroacetyl-N-(2,6-diethylphenyl)-glycineethylester to said 2,4-bis(ethylamino)-6-methylthio-1,3,5-triazine is about 8:4.5.

14. Method of claim 12, wherein said N-chloroacetyl-N-(2,6-diethylphenyl)-glycineethylester is applied at a level of 1-30 g/a, and said 2,4-bis(ethylamino)-6-methylthio-1,3,5-triazine is applied at a level of 3-10 g/a.

15. Method of claim 14, wherein said levels are 4-12 g/a and 4-8 g/a, respectively.

16. Method of claim 12, wherein the total level of active ingredients applied to said fields is at a level of 8-20 g/a.

* * * * *